US005257985A

United States Patent [19]

Puhl

[11] Patent Number: 5,257,985

[45] Date of Patent: Nov. 2, 1993

[54] MULTI-CHAMBER INTRAVENOUS BAG APPARATUS

[76] Inventor: Richard Puhl, 6125 - 241st Ave., Paddock Lake, Wis. 53168

[21] Appl. No.: 664,635

[22] Filed: Mar. 4, 1991

Related U.S. Application Data

[63] Continuation of Ser. No. 447,535, Dec. 7, 1989, abandoned, which is a continuation of Ser. No. 445,567, Dec. 4, 1989, abandoned.

[51] Int. Cl.[5] .......... A61M 37/00

[52] U.S. Cl. .......... 604/410; 604/408; 206/221

[58] Field of Search .......... 604/410, 416, 403, 408, 604/409, 411, 415; 206/219, 221, 438

[56] References Cited

U.S. PATENT DOCUMENTS

| | | | |
|---|---|---|---|
| 2,756,874 | 7/1955 | Erickson et al. | 383/38 |
| 2,848,995 | 8/1958 | Ryan | 604/408 |
| 3,082,867 | 3/1963 | Gelpey | 383/38 |
| 3,141,221 | 7/1964 | Faulis, Jr. | 24/462 |
| 3,149,943 | 9/1964 | Amador | 206/221 |
| 3,257,072 | 6/1966 | Reynolds | 604/410 |
| 3,639,952 | 2/1972 | Thompson et al. | 24/255 BC |
| 3,809,224 | 5/1974 | Greenwood | 206/219 |
| 4,529,102 | 7/1985 | Quinn et al. | 222/94 |
| 4,556,290 | 1/1971 | Popkin-Clurman | 206/47 |
| 4,559,053 | 12/1985 | Porges | 604/408 |
| 4,608,403 | 8/1984 | Larkin | 604/410 |
| 4,731,053 | 3/1988 | Hoffman | 604/410 |

FOREIGN PATENT DOCUMENTS

| | | | |
|---|---|---|---|
| 1437179 | 3/1966 | France | 206/221 |

*Primary Examiner*—Robert A. Hafer

*Assistant Examiner*—Sam Rimell

*Attorney, Agent, or Firm*—Jansson & Shupe, Ltd.

[57] ABSTRACT

An improved multi-chamber intravenous bag apparatus including a collapsible bag forming a chamber of substantially non-reduced cross-dimension along the entire bag. The device includes a pinching mechanism extending across the entire bag to create two subchambers, such mechanism preferably having interengageable male and female members. Fluid may be added to each subchamber and combined upon removal of the clamp. The device promotes quick, efficient, and economical fixing and administration of fluids.

9 Claims, 5 Drawing Sheets

MULTI-CHAMBER INTRAVENOUS BAG APPARATUS

RELATED APPLICATION

This application is a continuation of patent application Ser. No. 447,535, now abandoned, entitled MULTI-CHAMBER INTRAVENOUS BAG APPARATUS, filed one Dec. 7, 1989, on an invention of Richard T. Puhl, which is a continuation-in-part of patent application Ser. No. 445,567, entitled CLAMP FOR MULTIPLE CHAMBERED BAG, filed on Dec. 4, 1989, in the names of Richard T. Puhl and Richard W. Grabenkort, now abandoned.

FIELD OF THE INVENTION

This invention is related generally to multi-chamber intravenous bag systems and, more particularly, to clamping mechanisms for isolating separate chambers of such intravenous systems for two or more component solutions which are mixed in such systems just prior to use.

BACKGROUND OF THE INVENTION

In many medical or clinical settings the delivery of intravenous solutions necessitates isolation of component solutions until immediately prior to patient injection. A common, widely-used component solution pair is aminosyn II/dextrose. This solution pair discolors if mixed prior to sterilization, making it unmarketable and unusable. Other component solution pairs include potassium phosphate/calcium gluconate, potassium phosphate/TPN electrolytes, and sodium phosphate/calcium gluconate. Upon standing over time each of the above solution pairs, once mixed, tend to form insoluble precipitates which render them useless for intravenous injection. Solution stability and effectiveness are insured by separation until just prior to use, followed by adequate mixing.

Early concern over such precipitation and discoloration fostered the use of multiple intravenous bags, each with its own delivery stream. Mixing component solutions in this manner solved these problems, but created others. Multiple intravenous bags necessitate extra accessory injection equipment and require that each be sterilized. The increased potential for mechanical failure and introduction of aseptic conditions, as well as difficult and time-consuming set-up procedures are the primary problems associated with this means of intravenous injection.

The search for an efficient, effective intravenous injection system meeting the requirements stated above has been an ongoing concern in the art. One approach, which has been used with certain success, involves the use of a multi-chamber bag system utilizing upper and lower chambers (chambers A and B, respectively) separated by a clamped, narrow constricture. Such multi-chamber bags of the prior art typically include a clothes-pin type clamp which is opened just prior to use, enabling the contents from chamber A to flow slowly and mix with that in chamber B. Once completed, the clamp closes off chamber A. The combined component solutions are then injected intravenously from chamber B. Such multi-chamber intravenous bag systems have eliminated the need for pre-measuring component solutions and have overcome the aforementioned precipitation and discoloration concerns.

However, the prior art has associated with it a number of significant problems and deficiencies. Most are related to constricted flow from an upper chamber into the lower, and result from the type of multi-chamber bag apparatus currently used.

One major problem is that component mixing is slow and inefficient. Typically, the component in chamber A must be, in large part, squeezed into chamber B. At the same time all air must be removed from chamber A. The result is an unnecessary expenditure of time and, almost without exception, wasted component through adherence to chamber walls. Precision mixing is difficult. Devices of the prior art which include the aforementioned clothes-pin type clamp also permit escape of air into the unused upper chamber. Such loss of air from the lower chamber tends to distort volumetric graduation of the lower chamber. As such, graduated delivery from chamber B is difficult.

Another significant concern with certain multi-chamber bag systems of the prior art is that, given the self-contained nature of chamber B, introduction of additional components into the multi-chamber system, as is often desirable, is difficult at best. Because of this, the prior art resorts to the use of one or more additional bags, hung beside the multi-chamber bag, each with its own delivery stream which must then be combined with other streams before patient injection. However, the mechanical and sterilization problems mentioned above remain. In some instances, addition of a third component to chamber B is possible, but with certain widely-used multi-chamber bags the amount which can be added is limited to about 10–20 milliliters because of the limited excess capacity in chamber B once the component from chamber A has been added.

Another significant problem is that once chamber A is emptied that portion of the bag is sealed off and no longer useful, resulting in an inefficient and costly use of materials.

Another significant problem is that assembly of multi-chamber bag systems of the prior art is very labor intensive necessitating the use and time of several individuals.

In summary, a considerable number of drawbacks and problems exist in the art relating to multi-chamber intravenous bag systems. There is a need for an improved multi-chamber intravenous bag apparatus to fully utilize the advantages of a multi-chamber intravenous bag system.

OBJECTS OF THE INVENTION

It is an object of this invention to provide an improved multi-chamber intravenous bag apparatus, overcoming the problems of the prior art, including those mentioned above.

It is an object of this invention to provide an improved clamping mechanism for multi-chamber intravenous bag systems.

Another object of this invention is efficiency in the assembly of multi-chamber intravenous bag systems.

Another object of this invention is to provide an improved clamp for multi-chamber intravenous bag systems allowing quick, easy, and efficient mixing of component solutions.

Another object of this invention is to provide an improved clamp for multi-chamber intravenous bag systems such that the entire bag may be used after mixing.

Another object of this invention is to provide an improved clamp for multi-chamber, intravenous bag systems such that additional components may be added, and mixed quickly and efficiently.

Another object of this invention is to provide an improved clamp for multi-chamber intravenous bag systems such that component solutions are utilized completely, without waste.

Another object of this invention is to provide an improved clamp for multi-chamber intravenous bag systems such that the entire bag may include useful, volumetric, graduated markings.

Another object of this invention is to provide an improved clamp for multi-chamber intravenous bag systems such that volumetric mixing and controlled delivery may be achieved with increased precision.

These and other important objects will be apparent from the descriptions of this invention which follow.

SUMMARY OF THE INVENTION

This invention is an improved multi-chamber bag apparatus clamp for intravenous use. The invention overcomes certain well-known problems and deficiencies, including those outlined above.

An important aspect of this invention is an improved clamping arrangement, including a preferred clamp configuration. The inventive arrangement allows medical personnel to mix and administer multiple-component intravenous solutions efficiently and economically, in a precise, controlled manner. Removal of the clamp permits complete transfer of one component solution into the other with thorough mixing. The entire bag may be used. Intravenous delivery at controlled, volumetric increments is thus possible.

This invention is a multi-chamber bag apparatus including (1) a collapsible bag with upper and lower edges and walls extending between them, such walls forming a chamber of substantially non-reduced cross-dimension along substantially the entire bag, and (2) pinching means which divides the chamber into two subchambers and blocks passage of fluid between such subchambers.

The walls have inner and outer surfaces. The pinching means is removably applied to the outer surfaces. Fluid in one subchamber is isolated from that in the other until combination is desired. Removal of the pinching mechanism recreates a chamber from the first and second subchambers.

In preferred embodiments, the pinching mechanism is a clamp comprised of two interengaging linear male and female members. In highly preferred embodiments, the female member is hollow and substantially C-shaped in cross section along its length, with two opposed parallel edges.

In highly preferred embodiments, the male member is solid with a round cross-section of dimension greater than the distance between the parallel edges of the female member. When the bag walls are appropriately placed between the male and female members, interengaging them divides the chamber into two subchambers. The male member is preferably longer than the female member to insure the bag walls are pinched across the entire chamber.

In highly preferred embodiments, the female member is made with a resilient material such that the parallel edges can be spread to engage the male member. In highly preferred embodiments, the male member is made of a rubber-like, resilient, bendable material such that it may be peeled from the female member during removal.

In highly preferred embodiments, the bag apparatus is configured and arranged such that removal of the pinching mechanism creates extra capacity for additional fluid. The upper edge of the bag has means for attachment of the male or female member (or both members) to it, after one is disengaged from the other, to minimize bag distortion throughout fluid delivery. That is, the bag hangs with a less distorted cross-sectional shape along its length.

As already noted, a multi-chamber intravenous bag system has certain advantages. The clamp of this invention allows those advantages to be more fully realized. Only one person is needed to assemble the intravenous bag system. The clamp is placed perpendicular to the length of the bag, at or near the midpoint if component solutions of approximately equal volume are used. As component volumes vary, the position of the clamp across the width of the bag may be adjusted accordingly. The bag is thus sealed and divided into two separate chambers. Component solutions may be added through entry tubes at either end of the bag.

The improved clamp remains in place with the bag filled and sterilized, until intravenous delivery is needed. To combine the component solutions, the male member of the clamp is simply peeled away from the female member and the bag surface. Previously separated chambers become one, allowing the full volume of one component solution to flow into the other. Complete dissolution of the entire volumes of the two components may be accomplished by several inversions of the bag.

Additional solutions, if needed, may then be added volumetrically and quickly through the entry tubes at either end of the bag. In the context of a nutritional intravenous bag system, a large volume of fat emulsion is typically added in this manner. Such addition is possible because of extra volume available once the original component solutions are mixed. The combined weight fills and extends the lower portion of the bag, creating extra excess capacity.

This invention allows all component fluids, including added fluids, to be contained within a single bag for intravenous injection. Because of this, volumetric markings on the bag allow controlled intravenous delivery with increased precision.

DETAILED DESCRIPTIONS OF THE PREFERRED EMBODIMENTS

Figure 1:
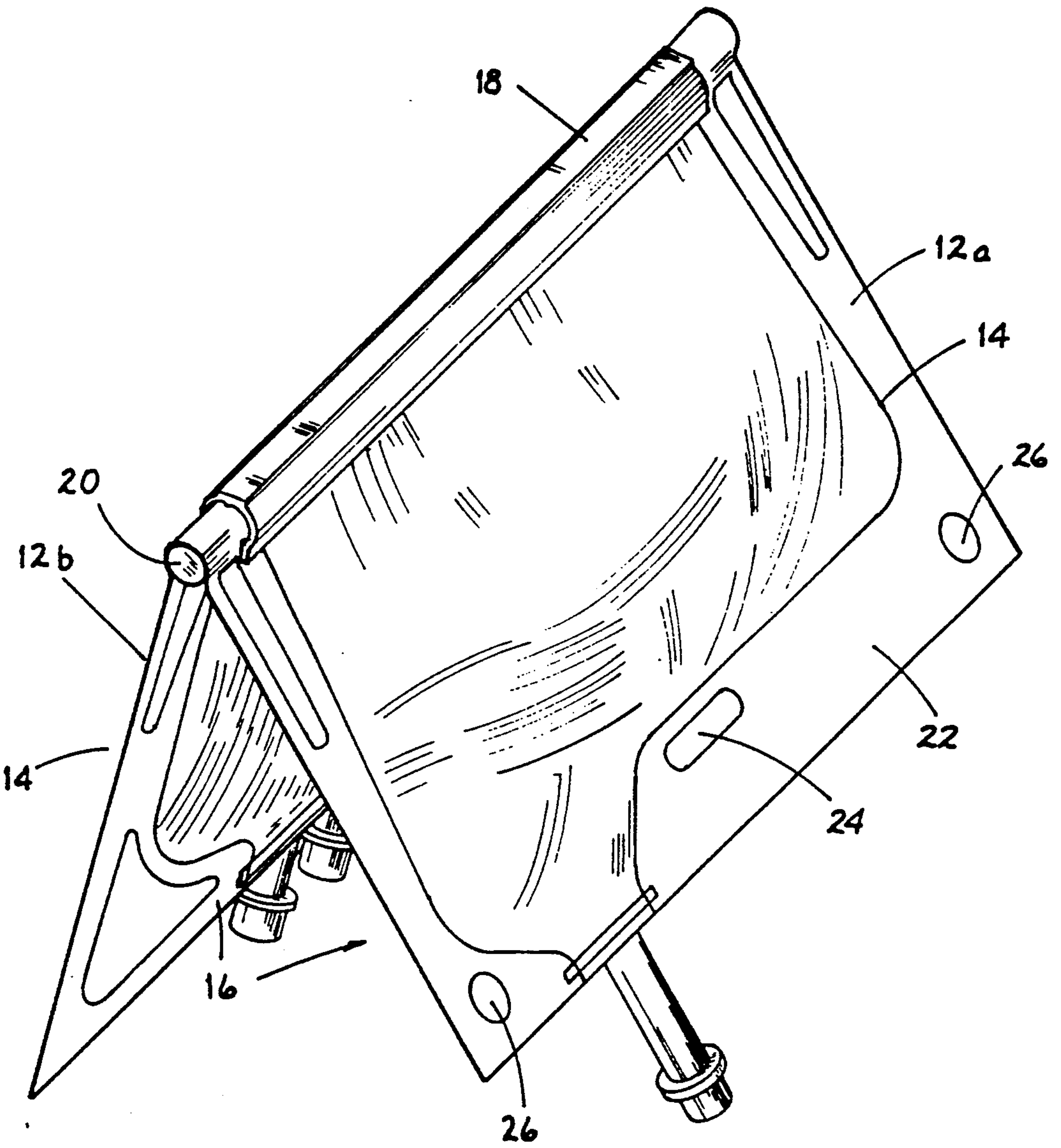
FIG. 1 is a full perspective view of a preferred improved multi-chamber intravenous bag apparatus in accordance with this invention.

The drawings illustrate an improved multi-chamber intravenous bag apparatus 10 which is a preferred embodiment of this invention. The apparatus includes a unqiue bag-clamp combination, including a bag 12, which is formed by first and second flexible sheets 14 and 16, and a clamp which has a female member 18 and a male member 20.

Figure 6:
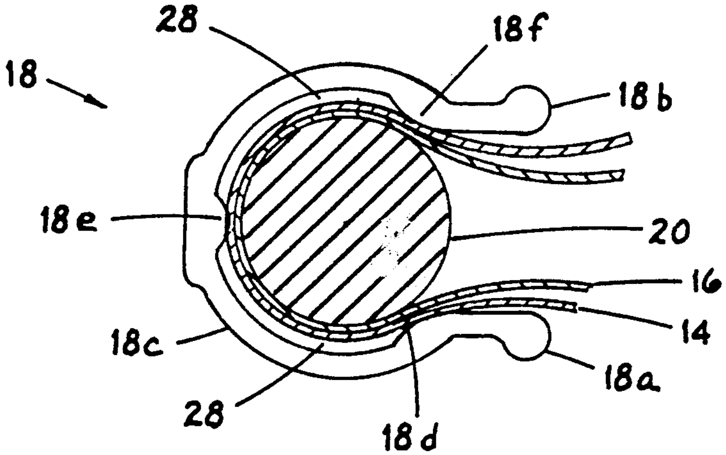
FIG. 6 is an enlarged fragmentary sectional view of an intravenous bag pinched between male and female members of the improved clamp.

As best shown in FIG. 6, female member 18 is comprised of a C-shaped portion 18*c*, which terminates in two straight edges 18*a* and 18*b* positioned parallel to each other and extending the length of the female member 18. The male member 20 has a diameter less than that of the C-shaped portion 18*c* of female member 18, and a length exceeding that of female member 18. In preferred embodiments, ridges 18*d*, 18*e*, and 18*f* are present on the inner surface of female member 18 and extend along its entire length.

As best shown in FIG. 6, male member 20 is positioned inside female member 18. First and second flexible sheets 14 and 16 of intravenous bag 12 are positioned and pinched between female member 18 and male member 20, with direct contact to both members along ridges 18*d*, 18*e*, and 18*f*. Inter-ridge spaces 28 permit complete sterilization of the multi-chamber intravenous bag system.

As shown in FIG. 1, the improved clamp and bag 12 form multi-chamber intravenous bag apparatus 10, having subchambers 12*a* and 12*b*. The improved clamp may be positioned anywhere along the width of bag 12 such that the desired volumes of the component solutions may be added to subchambers 12*a* and 12*b*. Each subchamber within delivery system 10 is defined by the position of the improved clamp, sealed edge 22, and first and second sheets 14 and 16 of bag 12. The improved clamp separates subchambers 12*a* and 12*b* and prevents component solution interaction until it is removed.

Figure 2:
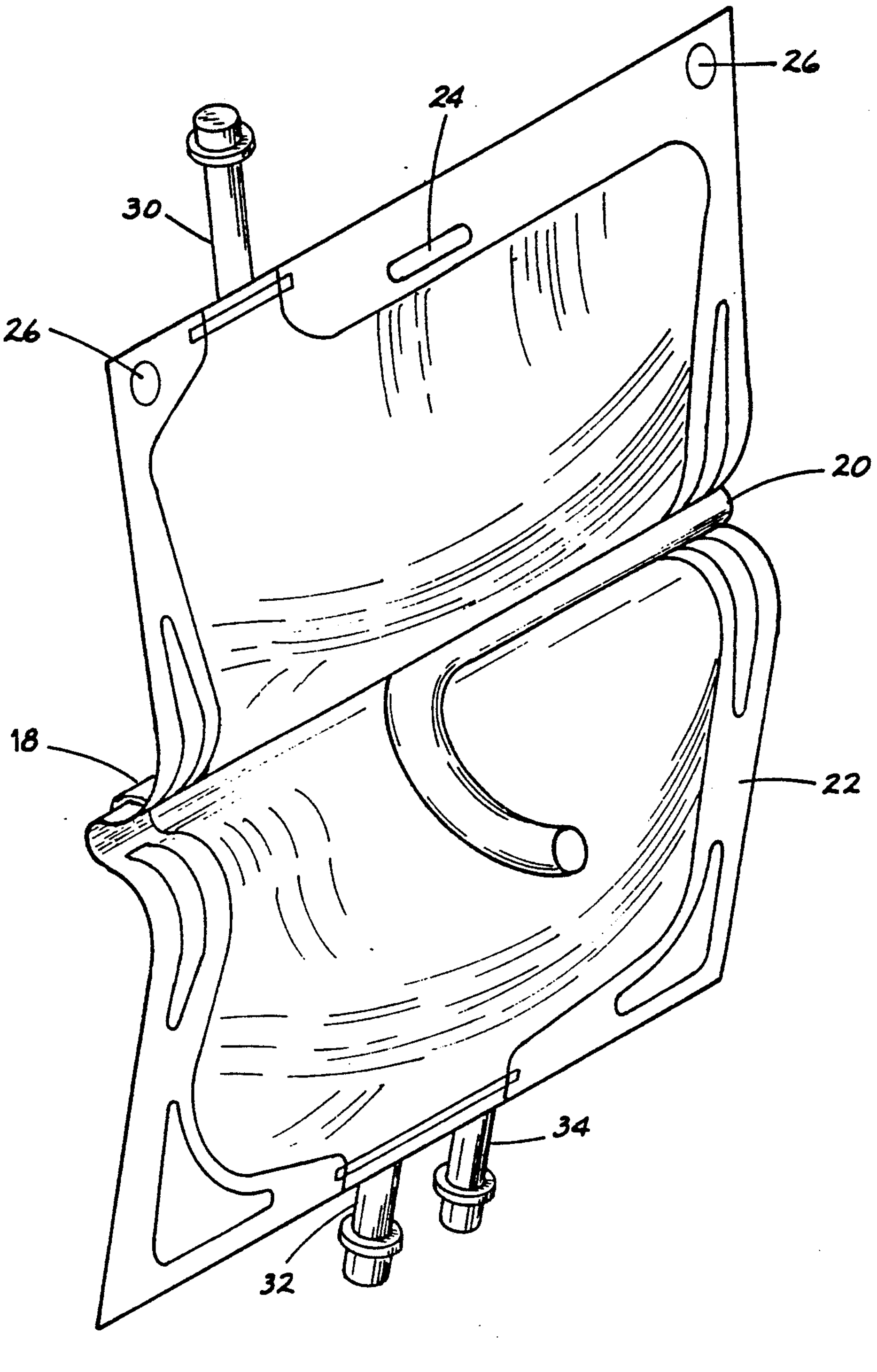
FIG. 2 is a perspective view of clamp removal.

As best shown in FIG. 2, male member 20 is pulled from female member 18. Once the improved clamp is fully removed the entire volumes of subchambers 12*a* and 12*b* flow into one another. Several inversions insure thorough and complete mixing. Additional solutions may be added through either the upper or lower entry tubes 30 and 32, respectively. Intravenous injection is accomplished through administration tube 34.

Figure 3:
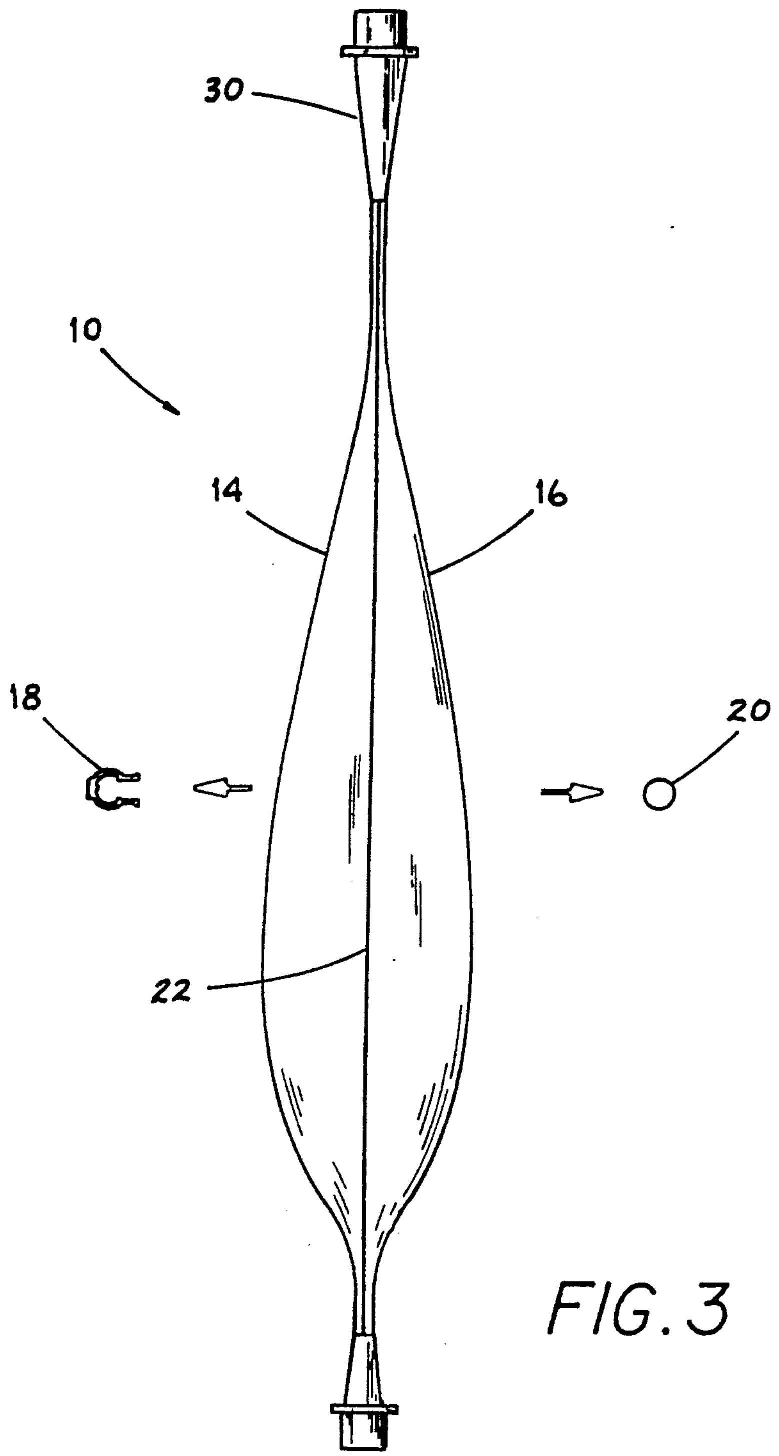
FIG. 3 is a side-edge elevation view of an intravenous bag, showing removed clamp parts off to the sides.

Upon removal of the clamp, the entire volumes of the component solutions are combined within a single chamber. As best shown in FIG. 3, the weight of a combined solution pulls downwardly on bag 12, creating extra volume capacity for additional solutions.

Figure 4:
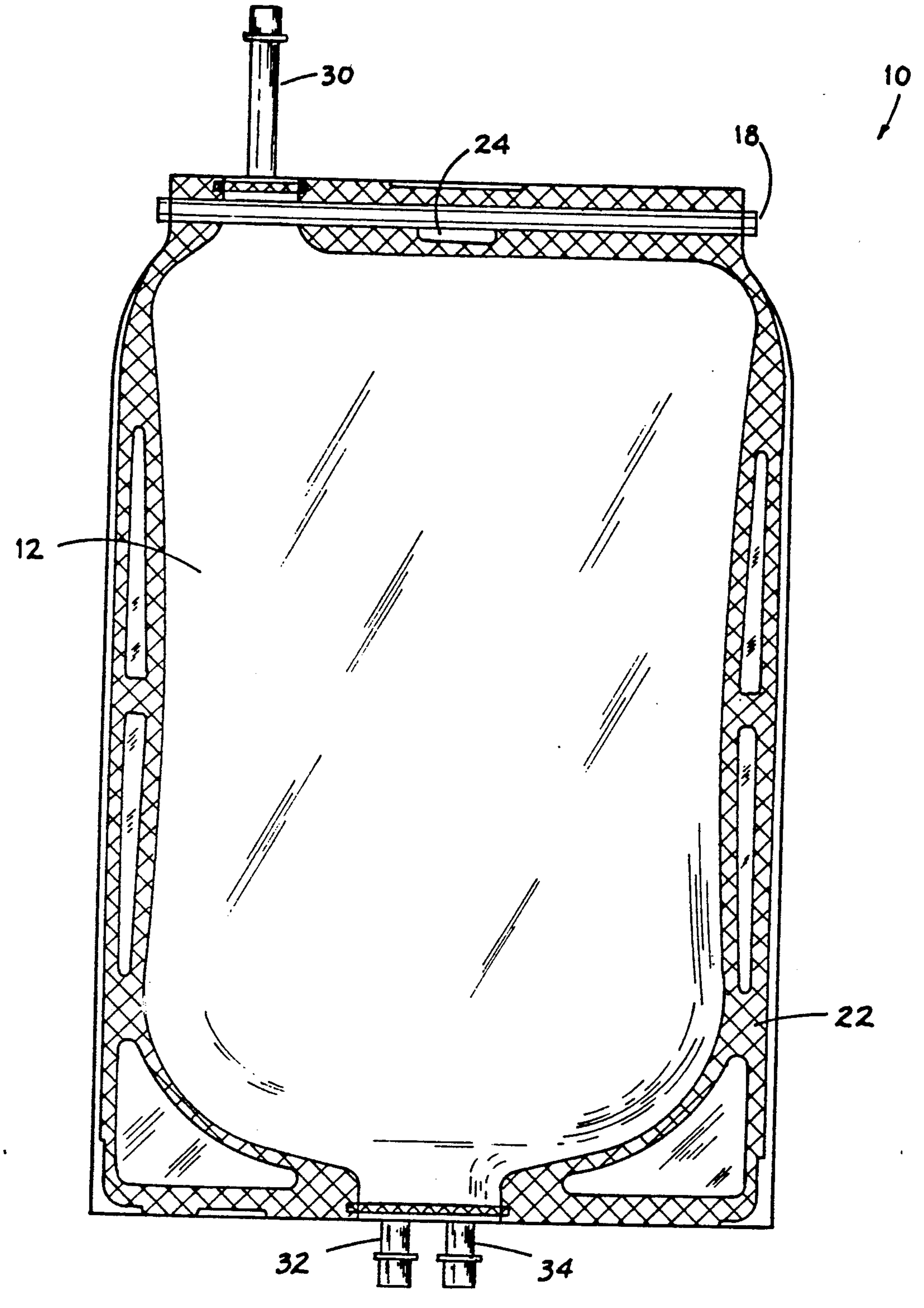
FIG. 4 is a face view of an intravenous bag with the female member of the improved clamp attached along the top of the bag.
Figure 5:
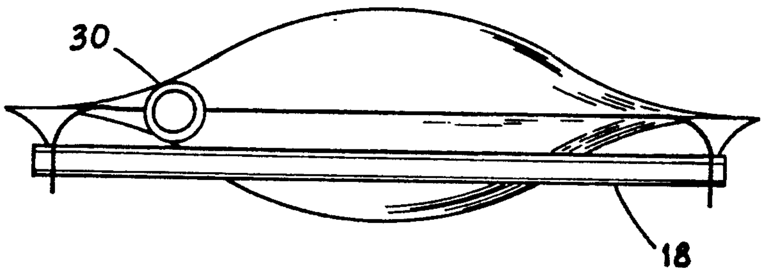
FIG. 5 is a top view of FIG. 4.

Intravenous administration is accomplished by attaching bag system 10 to an appropriate support through hole 24. As shown in FIGS. 4 and 5, female member 18 may then be positioned through upper corner holes 26 as added support against the weight of the combined component solutions. Utilization of female member 18 in this manner promotes an efficient use of materials and prevents too much distortion of the volumetric graduations on bag 12.

Female member 18 may be made using a variety of materials. Preferred materials include carbon composites, spring steel, hard rubber, wood, nylon, and rigid plastics with high-impact strengths. Aluminum is highly preferred, and acceptable for medical use.

A highly preferred embodiment of male member 20 is a solid rod, although hollow tubes could be used in some cases. Male member 20 may be made using a variety of materials. Preferred materials include medical-grade silicones, rubber, carbon composites, steel, nylon, aluminum, hemp, as well as various other plastics.

Bag 12 may be made using a variety of materials. Preferred materials include polystyrene, polypropylene, and other polyolefin plastics, as well as laminated aluminum foils. A polyester plastic blend is highly preferred and acceptable for medical use.

Acceptable material choices for these parts of the invention will be apparent to those skilled in the art who are made aware of this invention.

This invention has been described in connection with intravenous bag systems. However, the invention has applications beyond those described above, including but not limited to food products and epoxy glue preparations.

While the principles of this invention have been described in connection with specific embodiments, it should be understood clearly that these descriptions are made only by way of example and are not intended to limit the scope of the invention.

I claim:

1. In a multi-chamber intravenous bag apparatus of the type including a collapsible bag and means to block passage of fluid between chambers, the improvement comprising:

-the collapsible bag having upper and lower edges and walls extending therebetween and forming a chamber of substantially non-reduced cross-dimension along substantially the entire bag, said walls having inner and outer surfaces; and -interengaging linear members removably engaging the outer surfaces across the chamber to pinch the walls together and divide the chamber into first and second subchambers, said subchambers containing separate medical fluids to be mixed just prior to intravenous injection, said linear members including:

-a female member which is hollow and substantially C-shaped in cross-section along its length and has opposed first and second parallel edges and an inner surface;

-a male member dimensioned to be force-fit between said parallel edges of the female member and thereby tightly received and held by said female member with said bag walls pinched therebetween; and -the female and male members having at least two spaced contact lines extending therealong at which said bag walls are pinched, said linear members defining a non-contact space along the female member inner surface between said contact lines thereby facilitating complete sterilization of the intravenous bag including along and between the contact lines of bag pinching, whereby the medical fluid in one subchamber is isolated from the medical fluid in the other until combination is desired, whereupon removal of the linear members recreates the chamber from the first and second subchambers, allowing quick and easy mixture of the two medical fluids.

2. The bag apparatus of claim 1 wherein the parallel edges of the female member are spaced from one another by a first distance and the male member is of cross-sectional dimension greater than said first distance.

3. The bag apparatus of claim 2 wherein the male member is a solid piece of substantially round cross-section.

4. The bag apparatus of claim 3 wherein the male member is of a rubber-like resiliently bendable material whereby it may be peeled away from the female member during said removal.

5. The bag apparatus of claim 3 wherein the female member is of resilient material such that the parallel edges can spread slightly for passage therebetween of the male member.

6. The bag apparatus of claim 5 wherein the male member is of a rubber-like resiliently bendable material whereby it may be peeled away from the female member during said removal.

7. The bag apparatus of claim 2 wherein the male member is longer than and extends beyond the female member thereby to assure engagement of the bag walls across the entire chamber and to facilitate grasping of the male member for withdrawal from the female member.

8. The bag apparatus of claim 2 wherein the upper edge of the bag has means thereon for attachment of one of the linear members to the bag along said upper edge after disengagement of the linear members from one another, thereby minimizing bag distortion throughout fluid delivery operations.

9. The bag apparatus of claim 1 wherein the first and second subchambers are substantially filled with said separate medical fluids and wherein the bag apparatus is configured and arranged such that removal of the pinching means creates extra excess capacity, whereby after said removal substantial additional amounts of additional medical fluid may be added just prior to intravenous injection.

* * * * *